United States Patent [19]

Kuragano et al.

[11] Patent Number: 4,968,846

[45] Date of Patent: Nov. 6, 1990

[54] METHOD FOR THE PREVENTION OF POST OXIDATION OF METHACROLEIN

[75] Inventors: Morimasa Kuragano, Sakai; Kozo Iwasaki, Yokohama; Yoshio Koyama; Takeshi Isobe, both of Takaishi; Hirozo Segawa; Katsuji Yoguchi, both of Niigata, all of Japan

[73] Assignees: Mitsui Toatsu Chemicals, Incorporated; Kyowa Gas Chemical Industry Company, Ltd., both of Tokyo, Japan

[21] Appl. No.: 217,849

[22] Filed: Jul. 12, 1988

[30] Foreign Application Priority Data

Jul. 24, 1987 [JP] Japan ................................. 62-183565

[51] Int. Cl.$^5$ .............................................. C07C 45/00
[52] U.S. Cl. ..................................... 568/479; 568/476
[58] Field of Search ......................... 568/471, 476, 479

[56] References Cited

U.S. PATENT DOCUMENTS 2,627,527  2/1953  Connolly et al. .................... 568/476

OTHER PUBLICATIONS

Masuhiko et al., Derwent Abstract of Japan, 62163v; May 27, 1974.

*Primary Examiner*—Bruce Gray
*Attorney, Agent, or Firm*—Oblon, Spivak, McClelland, Maier & Neustadt

[57] ABSTRACT

This invention provides a method for the prevention of oxidation of resulting methacrolein immediately after its discharge from a reaction tube upon production of the methacrolein by vapor-phase oxidation of isobutylene, tertiary butanol or methallyl alcohol with a molecular-oxygen-containing gas in the presence of a catalyst. An inert gas and/or recirculated reaction gas or a mixed gas of an inert gas and/or recirculated reaction gas and air is fed and mixed with a reaction product gas immediately after an outlet of the reaction tube.

9 Claims, 1 Drawing Sheet

FIG.1
FIG.2
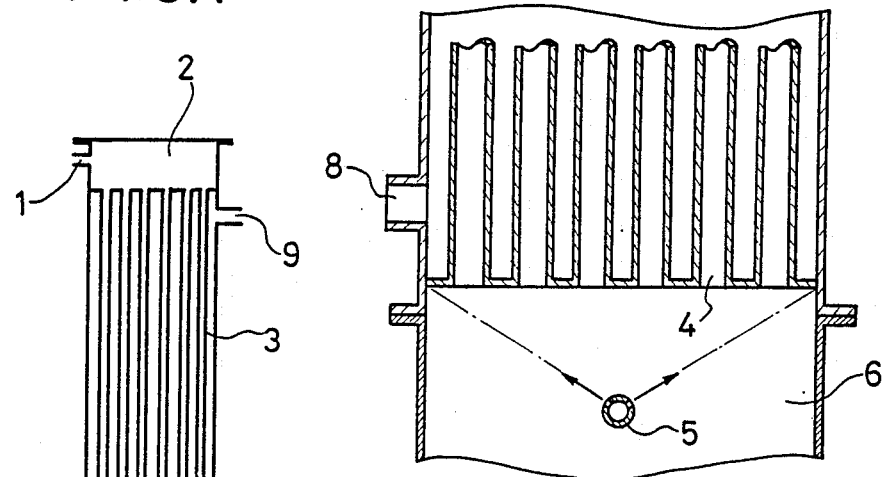
FIG.3
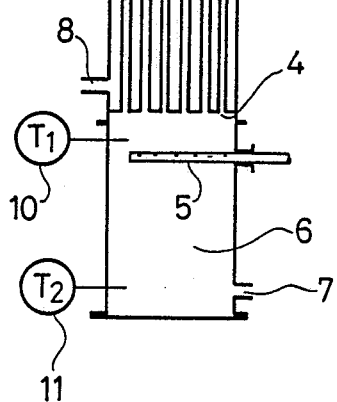
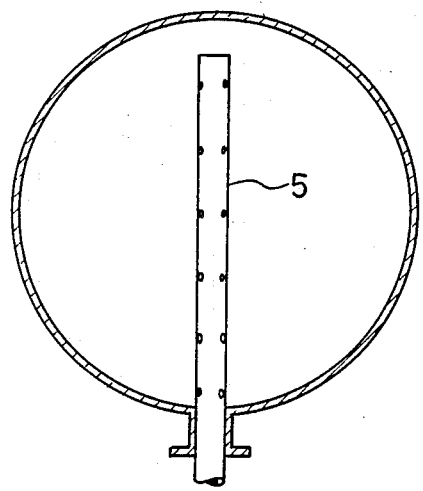

METHOD FOR THE PREVENTION OF POST OXIDATION OF METHACROLEIN

BACKGROUND OF THE INVENTION (1) Field of the Invention:

This invention relates to a method for the prevention of post oxidation of methacrolein.

(2) Description of the Prior Art:

Methacrylic acid is generally produced by a process, which comprises a former-stage reaction and a latter-stage reaction. In the former-stage reaction, isobutylene, tertiary butanol, methallyl alcohol or the like is used as a starting material. In the presence of an oxidation catalyst of the molybdenum-bismuth-iron system, the starting material is subjected at 300°–450° C. to vapor-phase oxidation with a molecular-oxygen-containing gas so that methacrolein is obtained primarily. In the latter-stage reaction, in the presence of a multi-element molybdate catalyst, the methacrolein obtained by the former-stage reaction is subjected at 250°–400° C. to vapor-phase oxidation with a molecular-oxygen-containing gas a in the former-stage reaction, whereby methacrylic acid is obtained.

In the former-stage reaction, a reaction product gas flowed out of a reaction tube at a high temperature of at least 300° C. as mentioned above is abruptly reduced in linear velocity in an empty column portion provided at an outlet of the reaction tube, so that oxidation of methacrolein with unreacted oxygen, which may be regarded as a post reaction, takes place to form carbon monoxide, carbon dioxide and the like.

The oxidation (hereinafter referred to as "post oxidation") of methacrolein with the unreacted oxygen leads to a decrease in the yield of methacrolein, whereby the yield of methacrylic acid from isobutylene, tertiary butanol or methallyl alcohol is lowered. It is hence necessary to prevent the post oxidation. For the prevention of the post reaction, it has been known effective to lower the temperature of a product gas immediately after the product gas has flowed out of the reaction tube. It has therefore been known to provide a cooler immediately after an outlet of a reaction tube or to spray water to an outlet portion of a reaction tube so as to cool the same (Japanese Patent Laid-Open No. 54317/1974).

When the cooler is provided at a location immediately downstream of the outlet of the reaction tube, the cooler is however assembled as a unitary element with the reactor so that the production facilities become complex and large and replacement of a catalyst or the like is rendered complex. In the spraying of water to the outlet portion of the reaction tube, the reaction product gas is prone to excessive over-cooling partially or locally so that high boiling substances, for example, terephthalic acid and trimellitic acid contained in the reaction product gas are caused to deposit, thereby causing their sticking on line walls or blocking of lines.

SUMMARY OF THE INVENTION

The present invention has been completed to solve the above problems. An object of this invention is therefore to provide an excellent method for the prevention of post oxidation of methacrolein.

In one aspect of this invention, there is thus provided a method for the prevention of post oxidation of methacrolein, which comprises feeding and mixing an inert gas and/or recirculated reaction gas or a mixed gas of an inert gas and/or recirculated reaction gas and air to and with a reaction product gas immediately after an outlet of a reaction tube upon production of the methacrolein by vapor-phase oxidation of isobutylene, tertiary butanol or methallyl alcohol with a molecular-oxygen-containing gas in the presence of a catalyst.

Owing to the present invention, methacrolein and methacrylic acid can be obtained efficiently by a method, which does not require complicated and scaled-up facilities and does not cool the reaction product gas abruptly, while preventing any substantial reduction in the yield of methacrolein and improving the unit in the production of methacrylic acid from isobutylene, tertiary butanol or methallyl alcohol as a raw material.

BRIEF DESCRIPTION OF THE DRAWINGS

FIG. 1 is a vertical cross-section illustrating one example of reactors useful in the practice of the method of this invention;

FIG. 2 is an enlarged fragmentary view of the exemplary reactor; and

FIG. 3 is a plan view of a sparger provided with the exemplary reactor.

In the drawings, there are shown a feed gas inlet 1, an upper empty column portion 2, reaction tubes 3, outlets 4 of the reaction tubes 3, the sparger 5, a lower empty column portion 6, an outlet 7 for a reaction product gas, a heating medium inlet 8, a heating medium outlet 9, and thermometers 10, 11.

DETAILED DESCRIPTION OF THE INVENTION

A fixed-bed oxidation column, which is employed commonly in processes for the production of methacrylic acid from isobutylene, tertiary butanol or methallyl alcohol as a raw material, can be used advantageously a reactor in the present invention.

As the fixed-bed oxidation reactor, a reactor in the form of a shell-and-tube heat exchanger such as that illustrated in FIG. 1 may be used by way of example. Each reaction tube packed with a catalyst is also packed at both end portions thereof with alundum (alumina balls) which is inert to the catalyst, feed gas and reaction product gas. The term "alundum" is a trade name for fused alumina ($Al_2O_3$) produced by the Norton Co. in the United States.

The term "inert gas" as used herein means, for example, nitrogen, carbon dioxide, steam or the like. By the term "recirculated reaction gas" as used herein, is meant a first gas which is a portion of a gas obtained after removing reaction products such as methacrolein and/or methacrylic acid from a former-stage and/or latter-stage reaction gas and is to be fed back to the reactor or a second gas which is obtained by mixing the first gas with the thus-separated methacrolein and is to be fed to the reactor.

The oxygen concentration in the mixed gas of the inert gas and/or recirculated reaction gas and air is up to 13 mole %, preferably 10 mole % so as to prevent the post oxidation of methacrolein.

The inert gas and/or recirculated reaction gas or the mixed gas of an inert gas and/or recirculated reaction gas and air (hereinafter referred to as "cooling gas"), which is fed to a point immediately downstream of the outlet of the reaction tube, is injected into and mixed with the reaction product gas, which has flowed out of the reaction tube, through an injection nozzles (hereinafter referred to a "sparger") provided with an empty column portion arranged immediately downstream of the outlet of the reaction tube. As a result, the flow of the reaction product gas is disturbed so that its temperature is lowered evenly and the possible post oxidation of methacrolein can be prevented.

The linear velocity (injection velocity) of the cooling gas injected from the sparger may preferably be at least twice the linear velocity of the reaction product gas (i.e., the linear velocity of the reaction product gas as expressed in terms of its velocity in the lower empty column portion. If the former linear velocity does not reach twice the latter linear velocity, it is impossible to disturb the flow of the reaction product gas to any sufficient extent so that uniform cooling effects can hardly be expected. An unduly high linear velocity of the cooling gas however wastes energy unnecessarily and moreover, causes a back flow of the reaction product gas to the reactor column and also gives influence of a pressure to the subsequent step (latter-stage reaction). Such an unduly high linear velocity cannot therefore achieve the above and other objects of this invention. Although the linear velocity of the cooling gas may be determined suitably in accordance with operational conditions of the process, a linear velocity 4–8 times the linear velocity of the reaction product gas is employed most preferably in general. Regarding the flow rate of the cooling gas, apparatus, piping and the like for the subsequent step or steps must be enlarged when the flow rate is too great while the disturbing effects for the flow of the reaction product gas are reduced when the flow rate is too small. The preferable flow rate ratio of the cooling gas to the reaction product gas is in a range of 0.1–3.0, with 0.3–1.5 being particularly preferred.

The temperature of the cooling gas to be injected into the reaction product gas may be adjusted in such a way that the temperature of the resulting mixed gas falls within a range of 200°–300° C. If the temperature of the cooling gas is too low to allow the resulting mixed gas to have at least 200° C., high boiling substances contained in the reaction product gas, for example, terephthalic acid, trimellitic acid and the like deposit on the wall of the empty column portion and cause blocking of piping and the like. On the other hand, any temperatures higher than 300° C. result in acceleration of oxidation of methacrolein in the mixed gas.

The shape and injection angle of the sparger provided in the empty column portion at a location immediately downstream of the outlets of the reaction tubes may be determined depending on the flow rate and linear velocity of the reaction product gas, the number of reaction tubes, etc. so as to permit efficient injection and mixing of the cooling gas for the attainment of the preferable temperature range of the mixed gas, for example, by arranging the sparger in the form of a ring, a plus sign (+) or a minus sign (−) inside the inner periphery of the empty column or by arranging a plurality of spargers. In particular, extremely good results may be obtained by injecting the cooling gas countercurrently against the flow of the reaction product gas.

One embodiment of this invention will hereinafter be described in detail with reference to the accompanying drawings.

FIG. 1 is the vertical cross-section of the reactor equipped with the sparger. FIG. 2 is the cross-section showing, on an enlarged scale, the outlet portions of the reaction tubes and the lower empty column portion in the reactor of FIG. 1. FIG. 3 is the drawing illustrating the sparger as viewed from the side of the outlets of the reaction tubes.

A feed gas, which has been supplied to the feed gas inlet 1 provided in an upper portion of the reactor and contains an inert gas, passes through the upper empty column portion 2 and then the reaction tubes 3 packed with a catalyst and controlled in temperature owing to circulation of a heating medium, so that the feed gas is subjected to an oxidation reaction to obtain a reaction product gas containing methacrolein. In the lower empty column portion 6 of the reactor, the flow of the reaction product gas is disturbed by a cooling gas jetted out from the sparger 5 provided in the lower empty column 6 at a location immediately downstream of outlets of reaction tubes. The temperature of the reaction product gas is lowered, whereby the loss of methacrolein due to its post oxidation is minimized. A portion of the resulting mixed gas which contains methacrolein in a high concentration is then recirculated as a cooling gas from the reaction product gas outlet 7 to the sparger 5. As an alternative, the resulting mixed gas is delivered in its entirety to the next step. In addition, the thermometers 10, 11 are provided inside the lower empty column 6 at a position between the sparger 5 and the outlets 4 of the reaction tubes and at another position near the outlet 7 for the reaction product gas, respectively. The temperature of the cooling gas is controlled on the basis of the thus-detected temperatures of the mixed gas, so that the resulting mixed gas can be controlled within a suitable temperature range.

[EXAMPLES]

This invention will hereinafter be described more specifically by the following Examples. It should however be borne in mind that this invention is not necessarily limited to the following Examples.

EXAMPLE 1

Employed as a reactor was a vertical shell-and-tube reactor equipped with 44 reaction tubes having a length of 4.0 m and an inner diameter of 21.4 mm as illustrated in FIG. 1. The inner diameter and length of an upper empty column portion were 340 mm and 300 mm respectively, while those of a lower empty column portion were 340 mm and 1,000 mm respectively. A sparger was provided at a location 100 mm the way down from outlets of reaction tubes. Each reaction tube was packed with a layer length of 400 mm of globular $Al_2O_3$, a layer length of 3,500 mm of a molybdenum-bismuth-iron catalyst, and a layer length of 100 mm of globular $al_2O_3$ successively in order from an inlet thereof. The sparger had such a structure that as illustrated in FIG. 2, a cooling gas could be evenly jetted out against a reaction product gas flowing out of the outlets of the reaction tubes. The sparger was provided with 12 injection holes of 15 mm in diameter, which were formed through a semi-cylindrical portion of the sparger on the side of the outlets of the reaction tubes.

Thermometers were provided near the outlet of one of the reaction tubes and the outlet for the reaction product gas respectively, thereby making it possible to measure the temperature of the mixed gas at both locations.

A feed gas containing isobutylene as a raw material and oxygen, steam and nitrogen as inert gases at a molar ratio of 1:2.5:5:15 was fed to a reactor, whose temperature was controlled at 360° C., to give an hourly space velocity of 1,800 hr$^{-1}$, whereby a reaction was conducted. Nitrogen and air, whose temperatures had been heated to 150° C., were mixed in proportions of 40 Nm$^3$/hr and 30 Nm$^3$/hr and injected through the sparger. The linear velocity of the reaction product gas at the outlet of each reaction tube was 2.09 m/sec. Results are shown in Table 1.

EXAMPLE 2

A reaction was conducted under similar apparatus, packing and reaction conditions as for Example 1. A recirculated reaction gas, which was composed of 88.0 mole % of nitrogen, 6.0 mole % of oxygen, 4.5 mole % of carbon dioxide, 1.5 mole % of steam, and air were mixed in proportions of 56 Nm$^3$/hr and 14 Nm$^3$/hr, preheated to 150° C., and then injected through the sparger. Results are shown in Table 1.

EXAMPLE 3

A reaction was conducted under similar apparatus, packing and reaction conditions as for Example 1. A recirculated reaction gas, which was composed of 55.0 mole % of nitrogen, 4.5 mole % of oxygen, 4.5 mole % of carbon dioxide, 31.5 mole % of steam and 4.5 mole % of methacrolein, and air were mixed in proportions of 50 Nm$^3$/hr and 20 Nm$^3$/hr, preheated to 150° C., and then injected through the sparger. Results are also shown in Table 1.

COMPARATIVE EXAMPLE 1

A reaction was conducted in the same manner as in Example 1 except that the cooling gas (150° C.) from the sparger was composed of 15 Nm$^3$/hr of nitrogen and 10 Nm$^3$/hr of air. Results are shown in Table 1. Post oxidation is believed to have taken place in view of the temperature increase in the empty column portion. The yield of methacrolein was reduced, while the yields of carbon monoxide and carbon dioxide increased.

COMPARATIVE EXAMPLE 2

A reaction was conducted in the same manner as in Example 1 except that the injection of the cooling gas from the sparger was stopped. Results are shown in Table 1.

Marked post oxidation is observed in view of the temperature increase in the empty column portion. The yield of methacrolein was reduced significantly.

empty column portion, reaction tubes and a lower empty column portion successively in order from an inlet thereof, the improvement comprising sparging a cooling gas at a linear velocity of 2-8 times the linear velocity of the reaction product gas as expressed in terms of its velocity at the lower empty column portion, into the lower empty column portion near the outlet of the reaction tubes, whereby the temperatures of the reaction product gas is reduced to 200°–300° C., the cooling gas being at least one of the following gases: (A) an inert inlet gas selected from the group consisting of nitrogen, carbon dioxide and steam or mixtures thereof; (B) a recirculated reaction gas which is a portion of a gas after removing a reaction product from the outlet gas of the reactor and which can be recirculated into the reactor; (C) a mixed gas of the inert gas (A) with air; or (D) a mixed gas of the recirculated reaction gas (B) with air; thereby preventing post oxidation of the methacrolein.

2. The method as claimed in claim 1, wherein the flow rate of the cooling gas is 0.1–3.0 times the flow rate of the reaction product gas.

3. The method as claimed in claim 1, wherein oxygen in the mixed gas of the inert gas or recirculated reaction gas with air is present in an amount up to 13 mole %.

4. The method as claimed in claim 1, wherein said cooling gas is further: (A) a gas obtained by separating methacrylic acid from the gas produced by subjecting the methacrolein to vapor-phase oxidation with a molecular oxygen-containing gas in the presence of a multielement molybdate catalyst; (B) a mixed gas of the gas (A) with methacrolein; or (C) a mixed gas of the gas (A) or (B) with air.

5. The method as claimed in claim 4, wherein the linear velocity of the cooling gas at the time of the blowing thereof is 2–8 times the linear velocity of the reaction product gas as expressed in terms of its velocity in the lower empty column portion of the reactor.

6. The method as claimed in claim 4, wherein the flow rate of the cooling gas is 0.1–3.0 times the flow rate of the reaction product gas.

7. The method as claimed in claim 4, wherein the temperature of the reaction product gas after the blowing of the cooling gas ranges form 200° C.–300° C.

8. The method as claimed in claim 1, wherein oxygen in the mixed gas of the inert gas or recirculated reaction gas with air is present in an amount up to 13 mole %.

TABLE 1

| | Linear velocity of cooling gas (m/sec) | Thermometer 1 (°C.) | Thermometer 2 (°C.) | Conversion of isobutylene (%) | Yield of methacrolein (%) | Yield of carbon monoxide (%) | Yield of carbon dioxide (%) |
|---|---|---|---|---|---|---|---|
| Ex. 1 | 9.0 | 255 | 220 | 99.5 | 83.5 | 4.0 | 4.5 |
| Ex. 2 | 9.0 | 257 | 223 | 99.4 | 83.6 | 4.0 | 4.4 |
| Ex. 3 | 9.0 | 256 | 222 | 99.4 | 83.4 | 4.2 | 4.4 |
| Comp. Ex. 1 | 3.3 | 305 | 302 | 99.6 | 74.2 | 4.9 | 5.6 |
| Comp. Ex. 2 | 0 | 320 | 330 | 99.6 | 72.1 | 5.6 | 6.8 |

We claim:

1. A method for the prevention of post oxidation of methacrolein prepared by the vapor-phase oxidation of isobutylene, tertiary butanol or methallyl alcohol with a molecular oxygen-containing gas in the presence of a molybdenum-bismuth-iron catalyst, by employing a vertical shell-and-tube reactor which has an upper 9. The method as claimed in claim 1, wherein said recirculated reaction gas (B) is a gas formed after removing a reaction project from the outlet gas of the reactor followed by adding a portion of thus removed methacrolein.

* * * * *